United States Patent
Rämsch et al.

(10) Patent No.: US 9,107,966 B2
(45) Date of Patent: Aug. 18, 2015

(54) METHOD FOR REDUCING THE VIRAL AND MICROBIAL LOAD OF BIOLOGICAL EXTRACTS CONTAINING SOLIDS

(75) Inventors: Christian Rämsch, Groβ Nordende (DE); Thomas Schräder, Uetersen (DE); Thomas Moest, Moorrege (DE); Manfred Kurfürst, Moorrege (DE)

(73) Assignee: Nordmark Arzeimittel GmbH and Co, KG, Uetersen (DE)

( * ) Notice: Subject to any disclaimer, the term of this patent is extended or adjusted under 35 U.S.C. 154(b) by 0 days.

(21) Appl. No.: 13/060,712

(22) PCT Filed: Aug. 27, 2009

(86) PCT No.: PCT/EP2009/006216
§ 371 (c)(1),
(2), (4) Date: May 23, 2011

(87) PCT Pub. No.: WO2010/022946
PCT Pub. Date: Mar. 4, 2010

(65) Prior Publication Data
US 2011/0268844 A1    Nov. 3, 2011

(30) Foreign Application Priority Data

Aug. 27, 2008 (DE) .................. 10 2008 039 860
Jun. 12, 2009 (EP) ..................... 09007797
Jun. 16, 2009 (WO) ................ PCT/EP2009/004318

(51) Int. Cl.
| C12N 9/00 | (2006.01) |
| A23L 1/305 | (2006.01) |
| A23L 1/28 | (2006.01) |
| A61L 2/00 | (2006.01) |
| C12N 9/94 | (2006.01) |
| A61K 38/00 | (2006.01) |

(52) U.S. Cl.
CPC .................. *A61L 2/0011* (2013.01); *C12N 9/94* (2013.01); *A61K 38/00* (2013.01)

(58) Field of Classification Search
CPC ......... A61L 2/0011; C12N 9/94; A61K 38/00
USPC ...................... 426/61, 645, 648, 655; 435/183
See application file for complete search history.

(56) References Cited

U.S. PATENT DOCUMENTS

| 2,189,948 A * | 2/1940 | Griffith et al. ................ 435/186 |
| 3,493,399 A | 2/1970 | Levin |
| 4,280,971 A | 7/1981 | Wischniewski |
| 4,623,624 A | 11/1986 | Schultze |
| 5,378,462 A | 1/1995 | Boedecker |
| 6,270,723 B1 * | 8/2001 | Laugharn et al. ................ 422/39 |
| 2003/0103863 A1 * | 6/2003 | Grislain et al. .................... 422/1 |
| 2005/0250817 A1 | 11/2005 | Shlieout |
| 2007/0148152 A1 | 6/2007 | Shlieout |
| 2011/0052706 A1 | 3/2011 | Moest |
| 2011/0268844 A1 | 11/2011 | Ramsch |
| 2012/0213857 A1 | 8/2012 | Moest |

FOREIGN PATENT DOCUMENTS

| CA | 394 981 A | 3/1941 |
| EP | 0436110 | 7/1991 |
| SU | 271472 | 7/1968 |
| WO | WO 00/48641 | 8/2000 |
| WO | WO 02/056824 | 7/2002 |
| WO | WO 2006/044529 A1 | 4/2006 |
| WO | WO 2007/014896 | 2/2007 |
| WO | WO 2008/127567 A1 | 10/2008 |
| WO | PCT/EP2009/006216 | 8/2009 |
| WO | PCT/EP2009/000566 | 12/2011 |

OTHER PUBLICATIONS

SU 271472—English Abstract—1971.*
Kingsley et al. 2002. J. Food Protection. No. 10; pp. 1605-1609. Abstract.*
International Search Report issued in corresponding international application PCT/EP2009/006216, mailed Oct. 14, 2009 (2 pages).
USPTO Office Action, mailed Jan. 13, 2012, issued in U.S. patent publication No. US 2011/0052706.
USPTO Office Action, mailed Mar. 23, 2012, issued in U.S. patent publication No. US 2011/0052706.
USPTO Office Action, mailed Jan. 7, 2013, issued in U.S. patent publication No. US 2011/0052706.
USPTO Office Action, mailed Nov. 27, 2012, issued in U.S. patent publication No. US 2011/0268844.
USPTO Office Action, mailed Mar. 14, 2013, issued in U.S. patent publication No. US 2012/0213857.

* cited by examiner

*Primary Examiner* — Hamid R Badr (74) *Attorney, Agent, or Firm* — Nash and Titus, LLC (57) ABSTRACT

The invention is a method for reducing the viral and microbial content of biological extracts which contain solids. The method comprises the steps of, (1), providing a biological extract which contains solids that comprise a biologically active substance, selected from enzymes, proteins and peptides, or a mixture of such substances; and (2) subjecting the biological extract to a high-pressure treatment; wherein the biological activity of the biological extract after the high-pressure treatment is at least 50% of the biological activity of the biological extract before the high-pressure treatment.

11 Claims, 6 Drawing Sheets

Fig. 1

PRIOR ART

METHOD FOR REDUCING THE VIRAL AND MICROBIAL LOAD OF BIOLOGICAL EXTRACTS CONTAINING SOLIDS

This application is a national filing based on PCT international application no. PCT/EP2009/006216, filed 27 Aug. 2009, and claims priority therefrom, as well as from Germany application no. DE 10 2008 039 860.8, filed on 27 Aug. 2008, European application no. EP 09007797.5, filed 12 Jun. 2009, and PCT international application no. PCT/EP2009/004318, filed 16 Jun. 2009, and the contents of all of these documents are incorporated in their entirety by reference.

FIELD OF THE INVENTION

The invention relates to a method for reducing the viral and microbial content of biological extracts which contain solids, a biological extract which contains solids which is produced using this method, and uses of such a biological extract which contains solids.

Extracts which are obtained from biological source material can have a high virus content. Viruses are nucleic acids which are surrounded by a protein shell. In the case of enveloped viruses there is another outer lipid envelope. As viruses cannot replicate independently, they are reliant on hosts. Accordingly they occur in virtually all living things in the world. Very few of the known viruses are pathogenic for humans, as they have a high host specificity. In order to rule out a hazard to consumers from the start, extracts which are intended for human consumption or are used as an active agent in medicaments should in principle have no virus content or one which is as low as possible. The actual production method does not always lead to a significant inactivation or removal of the viruses present so that, in particular in the production of pharmaceutical active agents, additional depletion or inactivation steps must be integrated into the method.

Numerous methods are known for the depletion or inactivation of viruses and micro-organisms. In addition to mechanical removal by for example chromatography or filtration, these contaminations can be inactivated selectively by adding chemical compounds. The latter method is however problematical in that these compounds must be removed again completely so that they do not cause any toxic effects in the end product. Physical methods such as heat treatment or irradiation are likewise usual methods for inactivating viruses or micro-organisms.

A particular challenge is the inactivation or removal of viruses from complex biological extracts whose active substances are enzyme mixtures, without destroying or changing the enzymatic activity of the proteins.

Of particular economic interest is the pharmaceutical active agent pancreatin, which is obtained as an extract from the pig pancreas and used in dried form as an oral therapeutic agent, as described in DE 3248588 A1.

Figure 1:
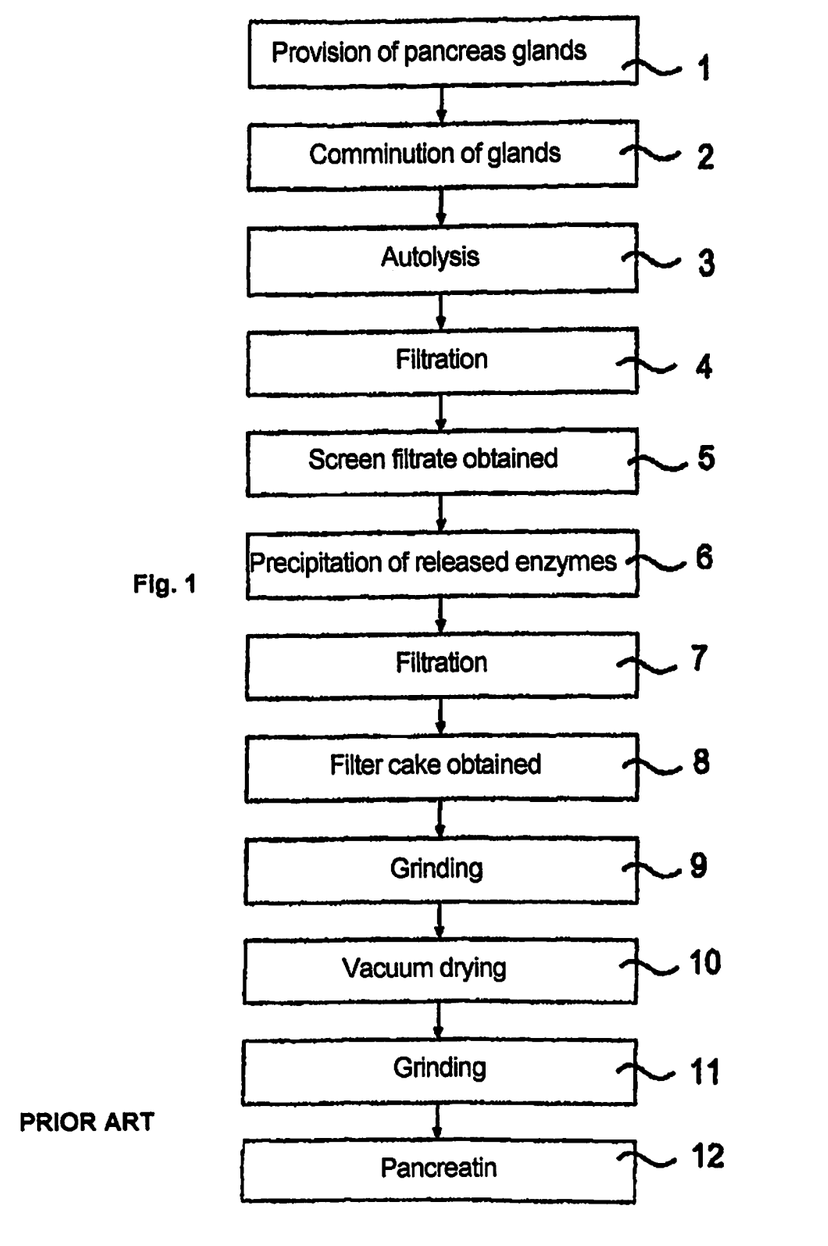
FIG. 1 shows a flow diagram of a method for producing pancreatin from porcine pancreas glands according to the prior art.

A typical method for producing pancreatin is described below with reference to FIG. 1. The pancreas glands 1 obtained from domestic pigs are first comminuted 2 and subjected to autolysis 3. The screen filtrate is obtained 5 by filtering 4 the intermediate product obtained in this manner. The enzymes which are in the screen filtrate are then precipitated out 6, the mixture is filtered 7, and the filter cake is obtained 8. The filter cake obtained is then ground 9, vacuum-dried 10 and ground again, as a result of which the pancreatin is obtained. The method steps labelled with the reference numerals 2 to 10 result in intermediate products, which are referred to below as intermediate stages.

The active substances in pancreatin include different enzymes which break down polymers, such as lipases, amylases and proteases. A prerequisite for the effectiveness of the therapeutic agent is that all the enzymes are present in the active agent in a certain ratio and in an active form. A particular feature of pancreatin is that the enzymes contained are present partially in solution and partially bound to particles, and it is thus a suspension.

Studies on the virus content of pancreatin have shown that enveloped viruses, but not unenveloped viruses, are significantly inactivated by the current production process. In principle, pharmaceutical active agents should contain no infectious viruses. Since the current production processes are apparently not able to remove potentially present contamination by unenveloped viruses with a sufficient safety margin, additional virus-reducing steps must be implemented.

Classical virus-inactivating methods such as dry or moist heat or virus-depleting methods such as filtration or chromatography cannot be used in most cases with extracts from biological source material and in particular with organ extracts without changes to the composition and/or high product losses. A particular problem of these extracts is often undissolved components, which give them a suspension-like quality. This leads to blocking of filters or chromatography columns. Furthermore, the active substances are often distributed both in the dissolved and in the particulate fraction and are thus partially removed by mechanical separation methods.

Further methods for inactivating viruses, bacteria and fungi in biological materials are known. For example, WO 02/056824 A2 describes the inactivation of pathogens in biological materials by using high pressure. The invention relates to the treatment of blood plasma, that is, to a solution of biological active substances in water. In "Pressure cycling technology: a novel approach to virus inactivation in plasma" (Transfusion, 40, 2000, 193), Bradley D. W. et al also describe a method for treating blood plasma.

The high-pressure treatment of foods has been described repeatedly. For example, mussels can be treated with high pressure in order to inactivate noroviruses or hepatitis A viruses (Kingsley et al., Inactivation of a Norovirus by High-Pressure Processing, Appl. Environ. Microbiol. 2007, 581; Calci et al., High-Pressure Inactivation of Hepatitis A Virus within Oysters, Appl. Environ. Microbiol. 2005, 339). The treatment is intended to preserve the organoleptic properties of the food. The biological activity of enzymes or other active substances after the high-pressure treatment has not been studied. Moreover, solids were studied in both cases.

It is however also known that it cannot easily be predicted whether inactivation of certain viruses using high-pressure treatment is actually successful (Grove S. F. et al., Inactivation of Foodborne Viruses of Significance by High Pressure and other Processes, J. Food Prot. 2006, 667). Different method conditions must be selected depending on whether the samples are liquid or solid owing to the different compressibility of the samples.

Moreover, the high-pressure treatment can result in a change in the food. For example, fruit turns brown if it is subjected to such a treatment. This colour change is due to an enzymatic reaction, which suggests a change in the biological activity of these enzymes.

A particular difficulty exists with biological samples which are not present in a largely homogeneous form. In an extract which contains solids in the form of a suspension, some of the biologically active substances are in the liquid phase, some are in the dispersed solids particles. An inactivation of viruses in the solids particles can therefore be connected with destruction of the active substances which are in the liquid phase, as the compressibility of the liquid phase is greater than that of the solids particles.

Pancreatin or the intermediate stages which occur during production constitute exemplary biological extracts which contain solids due to their natural virus content and their suspension quality. In classical spiking experiments, the corresponding substance is spiked with various laboratory strains, and the titer is determined before and after treatment.

There is furthermore a demand for methods in which the viral and bacterial content in a biological extract which contains solids is reduced completely or to a minimum. The method must be equally suitable for solids and suspensions. The method should in particular make possible the inactivation of unenveloped viruses in pancreatin.

SUMMARY OF THE INVENTION

The object of the invention is to eliminate the disadvantages of the prior art. In particular, a method for reducing the viral and microbial content of biological extracts which contain solids is to be specified, which is suitable for solids and suspensions, does not reduce the activity of the enzymes contained in the biological extract, does not impair the pharmacologically desirable properties and does not produce any toxic chemical compounds. Furthermore, extracts produced by means of the method and uses of the extracts are to be specified.

This object is achieved by the invention described herein.

According to the invention a method for reducing the viral and microbial content of biological extracts which contain solids is provided, comprising the steps
(a) provision of the biological extract which contains solids, comprising at least one biologically active substance, selected from enzymes, proteins and peptides, or a mixture of such substances; and
(b) subjecting the extract provided in step (a) to a high-pressure treatment;
wherein the biological activity of the biological extract which contains solids after the high-pressure treatment is at least 50% of the biological activity of the biological extract which contains solids before the high-pressure treatment.

A further method according to the invention for reducing the viral and microbial content of biological extracts which contain solids without reducing the activity of the enzymes contained in the biological extract comprises the following steps:
(a) pancreas glands obtained from domestic pigs are comminuted and subjected to autolysis;
(b) filtration of the intermediate product obtained according to step (a) in order to obtain a screen filtrate;
(c) subjecting the screen filtrate to a high-pressure treatment of 4000, 5000 and 6000 bar, preferably for 5 min. at 15° C.;
(d) precipitation of the enzymes contained in the screen filtrate;
(e) filtration of the mixture of step (d) in order to obtain a filter cake;
(f) subjecting the filter cake obtained according to step (e) to a high-pressure treatment of 4000, 5000 and 6000 bar, preferably for 5 min. at 15° C.;
(g) grinding the filter cake obtained according to step (f) with subsequent vacuum drying and repeated grinding to obtain the pancreatin.

The biological extract which contains solids is preferably provided as a suspension comprising a liquid phase and solid particles dispersed therein, wherein the mixture of biologically active substances is partially dissolved in the liquid phase and partially bound to the solid particles. The biological extract which contains solids can likewise preferably be provided in a solid form.

The term "biological extract which contains solids" in this case means an extract which comprises a biologically active substance, selected from enzymes, proteins and peptides or a mixture of such substances. It is preferred for the biological extract which contains solids to comprise a mixture of the said biologically active substances. For the sake of simplicity, the biological extract which contains solids is also referred to below as extract.

The biological extract which contains solids is preferably an extract which has been obtained as an alcoholic or aqueous extract from animal organs. The biologically active substance or mixture of substances contained can be present in the extract both in solution and bound to solids. A biological extract which contains solids of this type is a complex extract. The biologically active substance or the mixture of such substances preferably has pharmaceutical activity.

The term "biologically active substance" means pharmaceutical substances and therapeutic substances. Biologically active substances in the sense of this invention are for example enzymes, proteins and peptides.

Examples of animal organs from which the extract can be obtained are the liver, the pancreas and the gastric mucosa.

Figure 2:
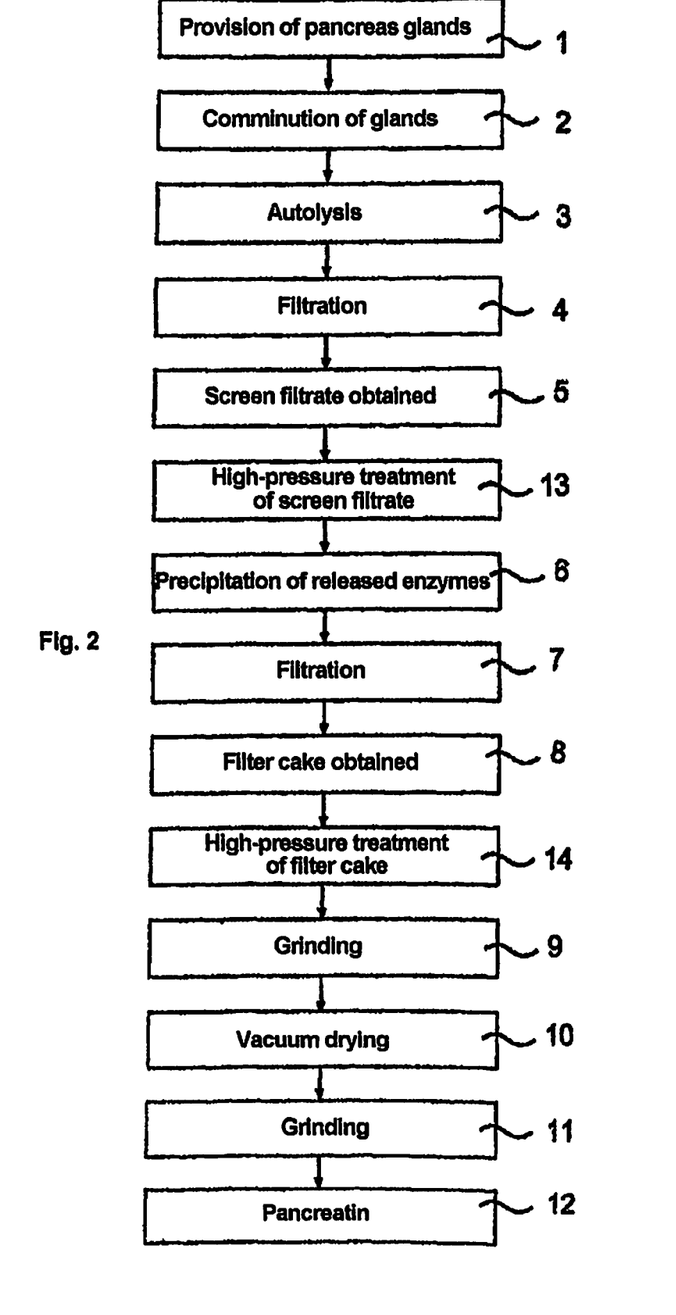
FIG. 2 shows a flow diagram of a method according to the invention for producing pancreatin from porcine pancreas glands.

Examples of biological extracts which contain solids according to the invention are extracts which are obtained from the pancreas, in particular the pancreas of the pig. Specific examples are pancreatin and the intermediate stages occurring during its production. These intermediate stages are indicated in FIG. 2 with the reference numerals 2 to 10. Preferred examples of these intermediate stages are the screen filtrate (reference numeral 5 in FIG. 2) and the filter cake (reference numeral 8 in FIG. 2), after the obtaining of which a high-pressure treatment is carried out, that is, the screen filtrate and/or the filter cake can be subjected to a high-pressure treatment (reference numerals 13 and 14 in FIG. 2). Pancreatin is obtained as a pharmaceutical active agent from the pancreas. Pancreatin and the intermediate stages occurring during production contain inter alia the enzymes lipase, amylase and protease. They are thus biological extracts which contain solids in the sense of the present invention. The extracts are preferably provided as aqueous/alcoholic extracts in step (a) of the method according to the invention.

The method according to the invention is applicable to all virus forms, such as DNA and RNA viruses, enveloped and unenveloped viruses, furthermore to virions and prions or similar biological systems and bacteria and fungi. The method is preferably used to reduce the content of unenveloped viruses in pancreatin from porcine pancreas or in corresponding intermediate stages occurring during production (see FIG. 2).

The method according to the invention allows the reduction of the virus and microorganism content of biological extracts which contain solids without their enzymic activity being substantially reduced, the pharmacologically intended properties being impaired or toxic chemical compounds being produced.

The biological activity of the biological extract which contains solids after high-pressure treatment should be at least 50% of the biological activity of the biological extract which contains solids before the high-pressure treatment, preferably at least 80%, particularly preferably at least 90%.

If one of the biologically active substances which are contained in the extract is an enzyme, then the enzymic activity of the biological extract which contains solids after the high-pressure treatment should be at least 50% of the enzymic activity of the biological extract which contains solids before the high-pressure treatment, preferably at least 80%, particularly preferably at least 90%.

The viral infectivity of the biological extract which contains solids after the high-pressure treatment should have been reduced by a factor of more than 1 $\log_{10}$, preferably more than 3 $\log_{10}$, particularly preferably more than 4 $\log_{10}$, compared to the viral infectivity before the high-pressure treatment. This also applies in particular to the viral infectivity of unenveloped viruses. For example, the infectivity of unenveloped viruses in pancreatin after treatment should be reduced by a factor of more than 1 $\log_{10}$, preferably more than 3 $\log_{10}$, particularly preferably more than 4 $\log_{10}$, compared to its infectivity before treatment. The germ content after the high-pressure treatment is preferably no more than 500 CFU/g, preferably no more than 100 CFU/g.

No chemical substances are added during the high-pressure treatment of the extract, so that the content of toxic substances after treatment is no higher than before treatment.

Step (b) of the method according to the invention is preferably carried out using pressures in the range from 1000 to 8000 bar, preferably in the range from 2000 to 7000 bar, particularly preferably in the range from 3000 to 6000 bar. The high-pressure treatment takes place according to the invention at a constant pressure or with pressure pulses and can be carried out continuously or in batches in corresponding apparatuses. The exposure time of the high-pressure treatment on the extract provided in step (a) is preferably 1 to 60 min. The high-pressure treatment is preferably carried out at temperatures between −20° C. and 30° C., particularly preferably between −10° C. and 20° C.

The liquid phase of the extract which is subjected to a high-pressure treatment in step (b) can contain water or a mixture of water and an organic solvent as the solvent. The solvent fraction can be in the range between 1 and 90% by weight in relation to the weight of the suspension. In the case of the biological extracts occurring during pancreatin production, the solvent used is preferably an alcohol, particularly preferably isopropanol. The isopropanol fraction is typically in the range between 5 and 85% by weight in relation to the weight of the suspension.

According to the invention, a biological extract which contains solids is furthermore provided which has been obtained by the method according to the invention. This extract is characterised by a low viral and microbial content. Despite the previous high-pressure treatment, its biological activity, in particular its enzymic activity is not substantially reduced, its pharmacologically intended properties are not impaired and it has no toxic chemical compounds which have been added during the treatment.

The extract according to the invention which is obtained by high-pressure treatment or the biological active substance produced therefrom can be used for the production of pharmaceuticals, in particular in the context of oral enzyme therapy, and as a foodstuff or nutritional supplement.

BRIEF DESCRIPTION OF THE FIGURES

The invention is explained in more detail below using examples, which are not intended to limit the invention, with reference to the drawings. In the figures.

DETAILED DESCRIPTION OF THE PREFERRED EMBODIMENTS

An embodiment of the method according to the invention for producing pancreatin is described below with reference to FIG. 2. The pancreas glands 1 obtained from domestic pigs are first comminuted 2 and subjected to autolysis 3. The screen filtrate is obtained by filtering 4 the intermediate product obtained in this manner. The screen filtrate can be subjected to a high-pressure treatment 13 before further treatment. The enzymes which are in the screen filtrate are then precipitated out 6, the mixture is filtered 7, and the filter cake is obtained 8. The filter cake obtained is subjected to a high-pressure treatment 14. The filter cake is then ground 9, vacuum-dried 10 and ground again, as a result of which the pancreatin is obtained 12.

According to the method shown in FIG. 2, a high-pressure treatment of the screen filtrate 13 or a high-pressure treatment of the filter cake 14 or a high-pressure treatment of the screen filtrate 13 and a high-pressure treatment of the filter cake 14 can be provided.

Example 1

The following example describes the treatment of intermediate stages from the pancreatin production process as biological extracts which contain solids and have been obtained from porcine pancreas with high pressure.
(1) Method
 The treatment was carried out in a high-pressure apparatus in a batch process.
a) An intermediate stage of the pancreatin production process (screen filtrate with approx. 5% by weight solids fraction in relation to the weight of the screen filtrate, see reference numeral 13 from FIG. 2) which was dissolved in 40% isopropanol was subjected to a high-pressure treatment at 4000, 5000 and 6000 bar for 5 min. at 15° C.
b) Alternatively, a high-pressure treatment was carried out under the same conditions with filter cake (see reference numeral 14 from FIG. 2, solids fraction approx. 50% by weight, liquid fraction consisting of approx. 80% by weight isopropanol and approx. 20% by weight water).

Figure 3:
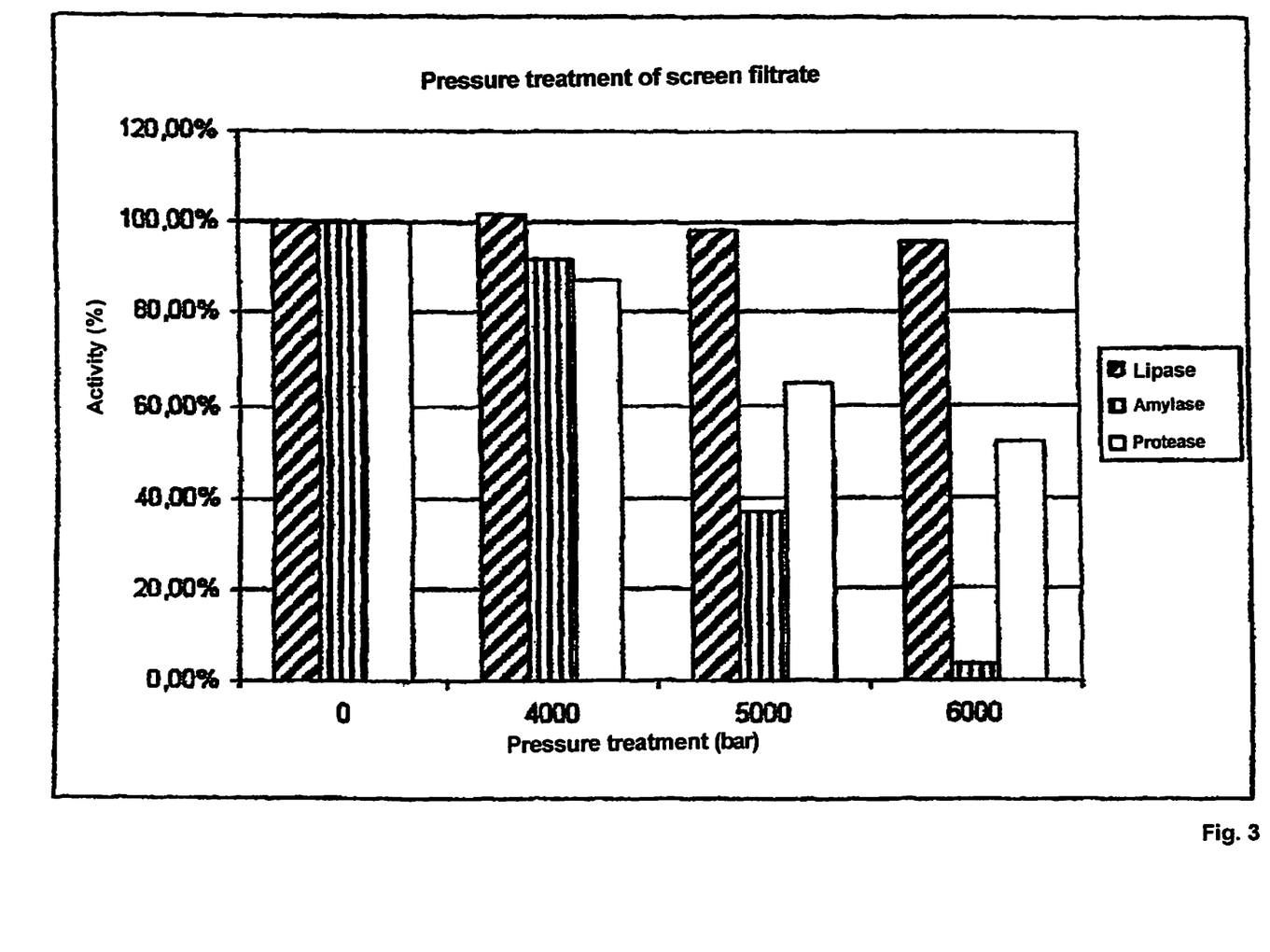
FIG. 3 shows a diagram which shows the relative enzymic activities after treatment of screen filtrate from the pancreatin production process with different pressures in percent, based on the starting activity of the untreated sample.
Figure 4:
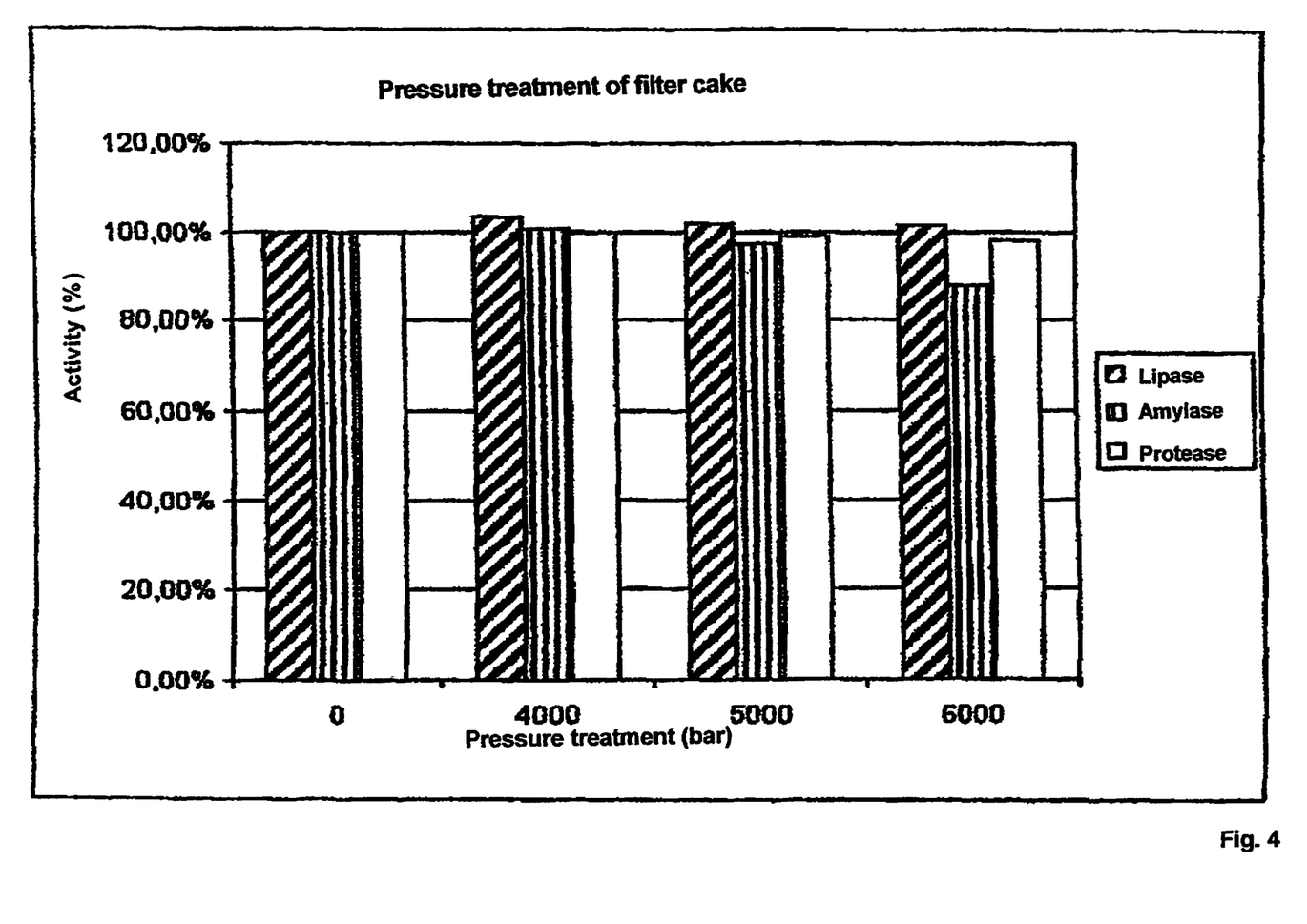
FIG. 4 shows a diagram which shows the relative enzymic activities after treatment of filter cake from the pancreatin production process with different pressures in percent, based on the starting activity of the untreated sample.

The activity of lipase, amylase and protease compared to an untreated sample was determined for both samples.
(2) Evaluation
 The results shown indicate that the three measured enzyme activities in the filter cake (FIG. 2) are not significantly reduced even with a high-pressure treatment of 6000 bar (FIG. 4). The lipase activity was also stable in the screen filtrate (FIG. 2) at all pressures. In contrast to this, the amylase activity in the screen filtrate was considerably reduced at pressures >4000 bar (FIG. 3).

Example 2

The following example describes the treatment of filter cake from the pancreatin production process which has been obtained from porcine pancreas with high pressure.

(1) Method

The treatment was carried out in a high-pressure apparatus in a batch process.

Filter cake (see reference numeral 14 from FIG. 2, solids fraction approx. 50% by weight, liquid fraction consisting of approx. 80% by weight isopropanol and approx. 20% by weight water) was subjected to a high-pressure treatment at various pressures and temperatures.

The activity of lipase, amylase and protease compared to an untreated sample was determined for all samples.

(2) Evaluation

Figure 5:
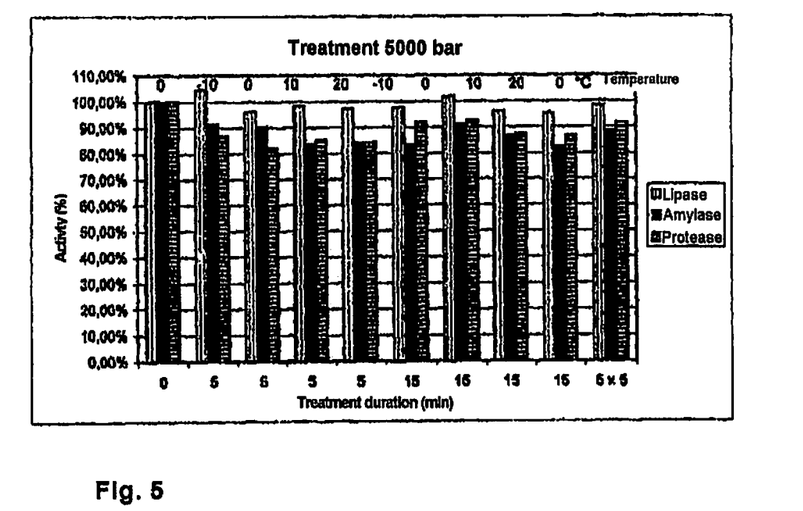
FIG. 5, FIG. 6 and FIG. 7 show diagrams which show the relative enzymic activities after treatment of filter cake from the pancreatin production process with different pressures and different temperatures in percent, based on the starting activity of the untreated sample.
Figure 6:
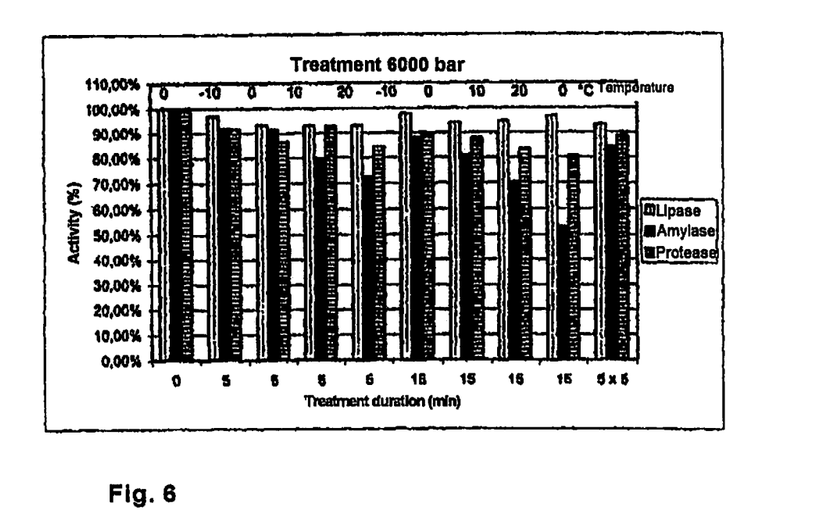
Figure 7:
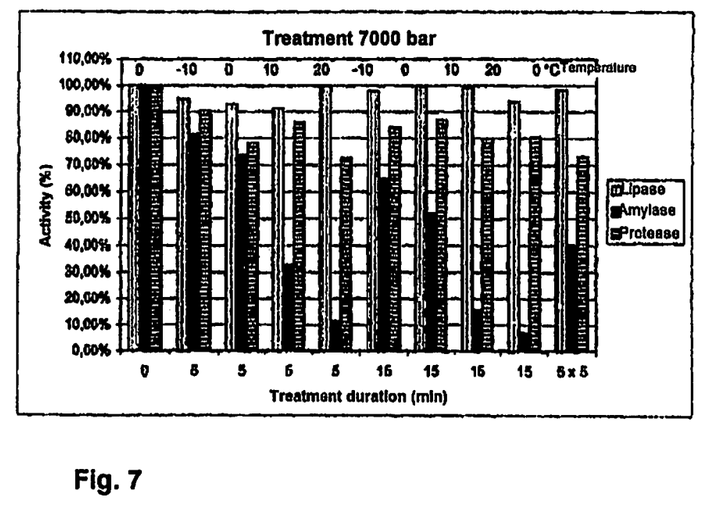

The results shown indicate that the inactivation of the enzymes in the filter cake (FIG. 2) depends both on the pressure and on the temperature. The lipase activity has the greatest stability and was not significantly inactivated even at pressures of 7000 bar (FIG. 5). In contrast to this, the amylase had the greatest sensitivity to high-pressure treatment. Low temperatures had a stabilising effect on the enzyme activities (FIG. 5).

Example 3

The following example describes the inactivation of the unenveloped virus FCV (feline calicivirus) using high pressure.

(1) Method

The treatment was carried out in a high-pressure apparatus in a batch process.

An FCV stock solution in culture medium was subjected to a high-pressure treatment at various pressures and temperatures for various times. The virus titer was determined in the starting sample and in the treated samples.

(2) Evaluation

The results shown (Tab. 1) indicate that the virus titer falls below the detection limit of 1.9 log due to the high-pressure treatment in all samples except the sample which was treated at 20° C., 5 min at 4000 bar. The difference between the virus titers of the untreated sample and the treated samples produces a depletion factor of ≥6.3 log. FCV is used as a model virus for the likewise unenveloped HEV, which has been found in pigs and is considered a human pathogen but cannot itself be detected in cell cultures. A depletion of this virus by >6 log stages represents a considerable improvement in the biological safety of pancreatin.

TABLE 1

Virus titers after high-pressure treatment of an FCV solution

| Treatment | | | | |
|---|---|---|---|---|
| Time (min) | Temperature (° C.) | 4000 bar | 5000 bar | 6000 bar |
| 0 | 20 | | 8.2 log | |
| 5 | 20 | 3.6 log | <1.9 log | <1.9 log |
| 5 | 20 | <1.9 log | <1.9 log | <1.9 log |
| 5 | 20 | <1.9 log | <1.9 log | <1.9 log |
| 5 | 0 | <1.9 log | <1.9 log | <1.9 log |
| 5 | 0 | <1.9 log | <1.9 log | <1.9 log |
| 5 | 0 | <1.9 log | <1.9 log | <1.9 log |
| 5 | −5 | <1.9 log | <1.9 log | <1.9 log |
| 5 | −5 | <1.9 log | <1.9 log | <1.9 log |
| 5 | −5 | <1.9 log | <1.9 log | <1.9 log |
| 15 | 0 | <1.9 log | <1.9 log | <1.9 log |
| 15 | 0 | <1.9 log | <1.9 log | <1.9 log |
| 15 | 0 | <1.9 log | <1.9 log | <1.9 log |

Example 4

The following example describes the inactivation of the unenveloped viruses FCV, EMCV (Encephalomyocarditis Virus) and Reo3 using high pressure.

(1) Method

The treatment was carried out in a high-pressure apparatus in a batch process.

The three viruses were spiked into the filter cake of the pancreatin production process and subjected to a high-pressure treatment at 6000 bar at various temperatures and for various times. The virus titer was determined in the starting samples (load samples), in the treated samples and in the untreated samples after carrying out the high-pressure treatment (hold samples).

(2) Evaluation

The results shown (Tab. 2) indicate that the titer of all the viruses studied was significantly reduced by the high-pressure treatment. For FCV a reduction factor of 3.82 log is produced. The two other viruses were reduced to a titer below the detection limit of 1.5 log. The corresponding load titers produce reduction factors of ≥4.98 log for EMCV and ≥3.78 log for Reo3. A reduction in the titer of these three zoonotic viruses (FCV=model for HEV) by more than 3.5 log stages represents a substantial improvement in the biological safety of pancreatin. With this experiment it could be demonstrated that the titer of various viruses in intermediate stages of the pancreatin production process can be significantly reduced by a high-pressure treatment. An optimal virus inactivation is achieved under the conditions which at the same time ensure maximum stability of the enzymes present in the pancreatin (temperatures ≤0° C.).

TABLE 2

Virus titers after high-pressure treatment of FCV, EMCV and Reo3 in the pancreatin filter cake.

| Treatment | | Titer (log $TCID_{50}$) | | |
|---|---|---|---|---|
| Temperature (° C.) | Duration (min) | FCV | EMCV | Reo3 |
| Load sample | | 6.97 | 6.48 | 5.28 |
| 0 | 5 | 4.76 | 2.97 | 2.97 |
| 0 | 15 | 5.77 | <1.5 | 2.88 |
| −10 | 5 | 4.35 | <1.5 | <1.5 |
| −10 | 15 | 3.15 | <1.5 | <1.5 |
| Hold sample | | 6.79 | 6.73 | 5.05 |

The exemplary embodiments likewise form the subject matter of the invention.

The invention claimed is:

1. A method for reducing the viral content of biological extracts which contain solids without reducing the activity of the enzymes contained in the biological extract, comprising the steps (a) providing a biological extract from an animal pancreas, which biological extract contains solids, comprising at least one biologically active substance, selected from the group consisting of enzymes, proteins and peptides, and a mixture of such substances; and (b) subjecting the extract provided in step (a) to a high-pressure treatment, for a duration of 1 to 60 minutes at a pressure of between 3000 to 6000 bar, wherein the biological activity of the biological extract which contains solids after the high-pressure treatment is at least 50% of the biological activity of the biological extract which contains solids before the high-pressure treatment, and wherein the biological extract which contains solids is provided as a suspension comprising a liquid phase and solid particles dispersed therein, and the suspension comprises at least 50% solids by weight wherein the mixture of biologically active substances is partially dissolved in the liquid phase and partially bound to the solid particles.

2. The method according to claim 1, wherein the biological extract in step (a) is obtained from pancreas glands from domestic pigs by the method comprising the steps of comminuting the glands and subjecting them to autolysis;

filtering the intermediate product obtained by autolysis in order to obtain a screen filtrate;

and wherein step (b) is carried out by the method comprising the steps of precipitating the enzymes contained in the screen filtrate;

filtering the product of precipitation in order to obtain a filter cake;

subjecting the filter cake obtained to the high-pressure treatment;

grinding the filter cake after high-pressure treatment with subsequent vacuum drying and repeated grinding to obtain pancreatin.

3. The method according to claim 1 wherein the biological extract which contains solids is obtained from the pancreas of the pig.

4. The method according to claim 1, wherein the biological extract which contains solids is subjected to a filtration step before the high-pressure treatment, as a result of which a filtrate and a filter cake are obtained, wherein the filter cake is subjected to the high-pressure treatment.

5. The method according to claim 1, wherein the biological activity of the biological extract which contains solids after the high-pressure treatment is at least 90% of the biological activity of the biological extract which contains solids before the high-pressure treatment.

6. The method according to claim 1, wherein the enzymatic activity of the biological extract which contains solids after the high-pressure treatment is at least 90% of the enzymic activity of the biological extract which contains solids before the high-pressure treatment.

7. The method according to claim 1, wherein the enzymatic activity of the biological extract which contains solids after the high-pressure treatment is >80% of the enzymic activity of the biological extract which contains solids before the high-pressure treatment.

8. The method according to claim 1, wherein the viral infectivity of the biological extract which contains solids after the high-pressure treatment has been reduced by a factor of more than 1 $\log_{in}$ compared to the viral infectivity before the high-pressure treatment.

9. The method according to claim 1, wherein the content of toxic substances in the biological extract which contains solids is no higher after the high-pressure treatment than before the high-pressure treatment.

10. The method according to claim 1, wherein after the high-pressure treatment the biological extract has a germ content of non-spore formers that is below the detection limit or less than 50 CFU/g.

11. The method according to claim 1, wherein the viral infectivity of the biological extract which contains solids after the high-pressure treatment has been reduced by a factor of more than 4 $\log_{10}$ compared to the viral infectivity before the high-pressure treatment.

* * * * *